United States Patent [19]
Johnson

[11] Patent Number: 5,484,873
[45] Date of Patent: Jan. 16, 1996

[54] TRIETHYLENEDIAMINE AND BICYCLIC AMIDINE BASED CATALYSTS AND USE IN THERMOSETTABLE COMPOITIONS

[75] Inventor: John R. Johnson, Danville, Ind.

[73] Assignee: Reilly Industries, Indianapolis, Ind.

[21] Appl. No.: 305,737

[22] Filed: Sep. 14, 1994

Related U.S. Application Data

[63] Continuation of Ser. No. 35,943, Mar. 23, 1993, abandoned.
[51] Int. Cl.$^6$ ............................ C08G 59/68; C08G 65/10
[52] U.S. Cl. ............................ 528/91; 528/118; 528/365; 525/506
[58] Field of Search ............................ 528/91, 118, 365; 525/506

[56] References Cited

U.S. PATENT DOCUMENTS 2,717,885  9/1955  Greenlee ................................... 528/91
2,839,495  6/1958  Carey ........................................ 528/91

FOREIGN PATENT DOCUMENTS 4817880  6/1973  Japan.

*Primary Examiner*—Frederick Krass
*Attorney, Agent, or Firm*—Woodard, Emhardt, Naughton, Moriarity & McNett

[57] ABSTRACT

Described are novel triethylenediamine adducts of certain 4-hydroxy-substituted, 3,5-hydroxy-substituted and 2,3,4-hydroxy-substituted benzoic acid derivatives, and novel boron trifluoride complexes with cyclic amidines, which are useful for the conversion of thermosettable compositions. Also described are novel thermosettable compositions incorporating the adducts and complexes.

8 Claims, No Drawings

TRIETHYLENEDIAMINE AND BICYCLIC AMIDINE BASED CATALYSTS AND USE IN THERMOSETTABLE COMPOITIONS

This application is a continuation of application Ser. No. 08/035,943, filed Mar. 23, 1993, now abandoned.

BACKGROUND

The present invention pertains to triethylenediamine adducts of certain benzoic acid derivatives and to boron trifluoride complexes with certain bicyclic amidines, and their use as catalysts in thermosettable compositions.

Thermosettable compositions are useful in many applications including for example their use as adhesive and coating compositions. Thermosettable compositions are largely based upon epoxy and/or anhydride and/or acid functionality. To prepare the thermosettable composition, the curable resin is blended with one or more catalysts. Depending upon the application, the catalyst can be designed to provide a fairly rapid cure after blending with the resin, or, the curing agent may be designed Co provide some measure of latency. That is, the thermosettable resin does not gel over a period of time, e.g. during storage, and only upon heating converts the resin from a liquid (or thermoplastic) state to a tough, hard thermoset solid.

Various compositions have been used as catalysts in thermosettable compositions. One group of curing agents includes certain complexes of Lewis acids and amines. For instance, U.S. Pat. No. 2,824,083 describes certain amine-$BF_3$ complexes used as curing agents for polyepoxies.

U.S. Pat. Nos. 4,933,422 and 4,614,788 describe the use of certain adducts of imidazoles with organic acids having $pK_a$ values of 0.5 to 5.0. U.S. Pat. No. 2,824,083 describes the use of $BF_3$ addition products with certain amines, amides, phenol or ether, dissolved in a liquid polyol such as a liquid polyalkylene glycol. U.S. Pat. No. 2,839,495 describes the use of the combination of an acid anhydride and a $BF_3$ complex such as a $BF_3$-amine complex to resinify polyepoxides.

U.S. Pat. No. 3,519,604 describes the use of a polycarboxylic acid anhydride and certain 3- or 4-amino pyridines in combination with a polyepoxy compound to form a curable composition.

Japanese KOKAI No. 64-3171A (Jan. 6, 1989) describes certain amino pyridine acid addition salts with dihydroxybenzoic acid derivatives, used as accelerators for curing epoxy resins.

Additional background information on catalysts and resins employed in thermosettable compositions can be found in U.S. Pat. Nos. 4,816,500 and 4,871,806 and European Patent Application Nos. 90308471.3 (Published Feb. 6, 1991) and 88119031,8 (Published May 24, 1989).

SUMMARY OF THE INVENTION

One preferred embodiment of the invention provides novel triethylenediamine adducts that are useful in preparing thermosettable compositions. The compounds of this preferred embodiment are triethylenediamine adducts of benzoic acid derivatives having the formula:

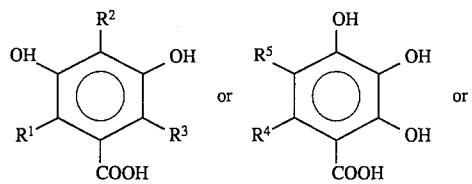

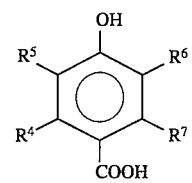

wherein $R^1$, $R^2$, $R^3$, $R^4$, $R^5$, $R^6$ and $R^7$, which can be the same or can be different from one another, are H, $C_1$ to $C_{10}$ alkyl phenyl; benzyl; halo; —$OR^8$ wherein $R^8$ is $C_1$ to $C_{10}$ alkyl or phenyl; —$COOR^9$ wherein $R^9$ is H, $C_1$ to $C_{10}$ alkyl or phenyl; or —$NR^{10}R^{11}$ wherein $R^{10}$ and $R^{11}$ can be the same or can differ from one another, are H or $C_1$ to $C_{10}$ alkyl.

Another preferred embodiment of the present invention provides a thermosettable composition. The thermosettable composition comprises a curable resin material, such as a resin having epoxy and/or anhydride and/or acid functionality, and a catalytic amount of a triethylenediamine adduct in accordance with the embodiment above.

Another preferred embodiment of the invention provides novel cyclic amidine/boron trifluoride complexes useful in preparing thermosettable compositions. The compounds of this preferred embodiment are boron trifluoride complexes with bicyclic amidine compounds having the general formula:

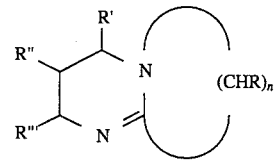

wherein n is a number ranging from 2 to about 11 and R, R', R" and R'", which may be the same or which may differ from one another, are H Dr lower alkyl.

Still another preferred embodiment of the invention provides a thermosettable composition which comprises a curable resin material and a catalytic amount of a $BF_3$/bicyclic amidine complex as described above.

Additional preferred embodiments of the invention include processes for preparing the compounds of the invention and for preparing and curing the above-specified thermosettable compositions.

The invention thus provides compounds that are useful as catalysts in thermosettable compositions, thermosettable compositions, and processes for their preparation and use. Additional embodiments, as well as features and advantages of the invention, will, be readily apparent from the following description.

DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention pertains.

The triethylenediamine (also sometimes referred to as TED, 1,4-diazabicyclo[2.2.2]octane, or Dabco) employed in the invention can be obtained commercially or by known processes utilizing readily available starting materials (see, e.g., Krause et al., British Patent 871,754 (1958)). The triethylene diamine is reacted with a benzoic acid derivative of the formula:

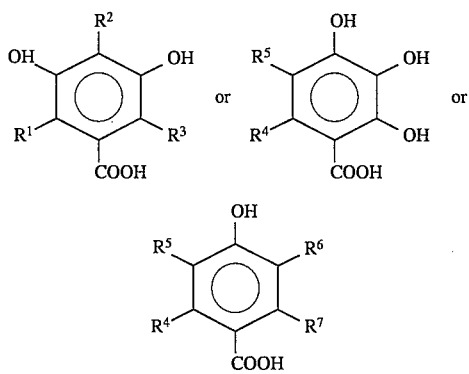

wherein $R^1$, $R^2$, $R^3$, $R^4$, $R^5$, $R^6$ and $R^7$, which can be the same or can be different from one another, are H, $C_1$ to $C_{10}$ alkyl; phenyl; benzyl; halo; —$OR^8$ wherein $R^8$ is $C_1$ to $C_{10}$ alkyl or phenyl; —$COOR^9$ wherein $R^9$ is H, $C_1$ to $C_{10}$ alkyl or phenyl; or —$NR^{10}R^{11}$ wherein $R^{10}$ and $R^{11}$ can be the same or can differ from one another, are H or $C_1$ to $C_{10}$ alkyl. The 4-hydroxy-substituted, 3,5-hydroxy-substituted or 2,3, 4-hydroxy-substituted benzoic acid derivatives employed in the invention may be obtained commercially or may be prepared using conventional techniques well within the purview of the ordinarily skilled artisan.

The triethylenediamine adducts can be prepared by reaction of triethylenediamine with the selected benzoic acid derivative so as to form the adduct. For example, The acid can be dissolved in a suitable solvent such as acetone, ethyl acetate or toluene. The triethylenediamine can then be added portionwise and the reaction promoted with heat. Water may be removed by azeotropic distillation when using toluene to form a dry solution. After cooling, the precipitated adduct can be recovered by filtration, washed,with solvent, and dried.

As specified above, other preferred embodiments of the invention include bicyclic amidine/boron trifluoride ($BF_3$) complexes and thermosettable compositions containing them in catalytic amount. The bicyclic amidine for use in the invention has the formula:

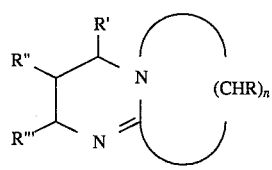

wherein n is a number ranging from 2 to about 11, preferably 3 to 7 and R, R', R" and R''', which may be the same or which may differ from one another, are H or lower alkyl (i.e. $C_1$ to $C_5$ alkyl). 1,5-Diazabicyclo[4.3.0]non-5-ene and 1,8-diazabicyclo[5.4.0]undec-7-ene are especially preferred bicyclic amidines for use in the present invention. The bicyclic amidines for use in the invention may be obtained commercially or may be prepared by techniques known to the art, including for example by the condensation and subsequent cyclization of mixtures of 1,3-propanediamine with pyrrolidone or caprolactam, (see, Hesse, M. et al., Chem. Ing. Tech., 63(10), pp. 1001–1003 (1991)), or by the catalyzed reaction of a lactam with an unsaturated nitrile (see, U.S. Pat. No. 4,943,633). The presence of other, non-interfering substituents on the rings of the bicyclic amidines will be acceptable for the invention and within the general spirit and scope thereof.

To prepare the $BF_3$/bicyclic amidine complexes, selected bicyclic amidines can be reacted with a suitable $BF_3$ source so as to provide their corresponding complexes. As an example, a flask can be charged with the bicyclic amidine as a 50 wt % solution in tetrahydrofuran. This solution can be cooled to 15° C., and an equimolar amount of $BF_3$ etherate added at such a rate that the reaction temperature does not exceed 20° C. The reaction mixture is stirred, e.g. for about one hour. The precipitated white solids can be filtered, washed, and dried.

Thermosettable compositions of the invention are prepared by blending a catalyst of the invention, a triethylenediamine adduct or a bicyclic amidine/$BF_3$ complex, as the case may be, into a curable resin material in the desired catalytic amount, typically about 1 to about 10 weight parts per 100 weight parts of resin. The curable resin material for use in the invention can for example contain epoxy functionality, and/or anhydride functionality and/or acid functionality, and have application in adhesive or coating compositions, among others. Where the catalyst has low solubility in the resin of interest, it is preferred to grind the catalyst to a small particle size prior to blending in order to assist in dispersing the catalyst in the resin. After its preparation, the thermosettable composition will be conventionally employed.

The catalysts of the invention may, of course, be used in the thermosettable composition in combination with other conventional additives, for instance curing agents such as phenol-novolac, cresol-novolac and 3,3'-diallyl-4,4'-dihydroxybisphenol A; amine compounds such as 4,4'-methylenebis(2-ethylaniline), 4'4-methylenebis(2,6-diethylaniline) and 4,4'-methylenebis(2-ethyl-6-methylaniline); acid anhydrides such as Nadic Methyl Anhydride (methyl-bicyclo [2.2.1]heptene-2,3 -dicarboxylic anhydride), phthalic anhydride, tetrahydrophthalic anhydride, methyltetrahydrophthalic anhydride, trimellitic anhydride, and pyromellitic anhydride; amide compounds such as dicyandiamide; and dihydrazide compounds such as adipic dihydrazide and isophthalic dihydrazide. Additional conventional additives include dyes, pigments, antioxidants, UV stabilizers, fillers, solvents, reinforcing materials and the like.

The following Examples are provided by way of illustration and not by way of limitation.

EXAMPLE I

Preparation of TED Adducts

The following procedure was used to prepare the adducts set forth and characterized below. A 1000 ml four-neck flask, equipped with a mechanical stirrer, thermometer, Dean Stark trap with condenser, and a powder funnel, was charged with the benzoic acid derivative (0.306 mole) and either acetone, ethyl acetate or toluene (600 ml). This mixture was warmed to 40° C. and the TED was added in portions through the powder funnel. A slight exothermic reaction occurs during the TED addition. After addition of all of the TED, the powder funnel was washed with solvent (50 ml) and replaced with a stopper. The reaction mixture was heated to reflux and the water removed by azeotropic distillation, when using toluene, until the solution was dry. A total of 50 ml of wet toluene was distilled off after no more water was detected coming over. The reaction mixture was then allowed to cool to room temperature. The precipitated solids were filtered, washed with solvent, and dried to give the desired TED adduct.

The following compounds were prepared as above:

TED-3,5-Dihydroxybenzoic Acid, m.p. 244–248 dec, Combustion analysis Actual (theory); C: 58.40 (58.64); H: 6.91 (6.81); N: 10.54 (10.52).

TED-2,3,4-Trihydroxybenzoic Acid, m.p. 180–185 dec, Combustion analysis Actual (theory); C: 55.45 (55.31); H: 6.48 (6.43); N: 9.85(9.92).

TED-Gallic Acid, m.p. 199–200, Combustion analysis Actual (theory); C: 55.16 (55.31); H: 6.44 (6.43); N: 9.86 (9.92); O: 28.35 (28.34).

TED-2 Gallic Acid, m.p.>200 dec, Combustion analysis Actual (theory); C: 53.21 (53.10); H: 5.37 (5.35); N: 6.20 (6.19).

TED-4-Hydroxybenzoic Acid, m.p. 195 dec, Combustion analysis Actual (theory); C: 62.46 (62.38); H: 7.32 (7.25); N: 11.12 (11.19).

EXAMPLE II

Testing of TED Adducts

The catalytic properties of the adducts prepared in Example I were evaluated as follows. The adducts were dispersed at 10 parts per 100 parts of resin (EPON 828, epoxy equivalent weight (EEW) about 185) along with 1.4% of a hydrophobic fumed silica rheology control agent. Dispersion was accomplished on 250 g batches of resin mix using a high shear disperser, or Dispermat CV equipped with a 20 mm blade and operated at 3000 rpm for a period of time sufficient to achieve adequate dispersion visually, generally about 3–6 minutes. Ratios of viscosity build were calculated at one and three day intervals by dividing the 1 and 3 day heat aged (at 55° C.) viscosity values by he initial viscosities. Longer term latency was measured by continuing to monitor viscosity build over time, with daily checks to monitor polymerization.

Gel times were tested on twenty gram portions of the above mixes in 18 by 150 mm test tubes, using a Sunshine gel meter equipped with a thermostatically controlled silicone oil bath. The oil bath permitted precise temperature regulation of the test sample to within plus or minus 0.2° C. Gelation is noted in this instrument by measurement of viscosity build during polymerization. At a predetermined viscosity point, a highly reproducible torque is registered by the instrument, i.e., gel point. The results of the Sunshine gel time (min.) and latency ratio testing are set forth in Table 1.

TABLE 1

| TED Adduct of | /--Sunshine Gel Time--/ | | Heat Aged (55° C.) Latency Ratio | |
|---|---|---|---|---|
| | 120° C. | 150° C. | 3 day | 1 day |
| Gallic Acid | 19.9 | 5.4 | 0.9 | 1.0 |
| 2,3,4-THBA | 14.1 | 5.3 | 1.11 | 0.98 |
| 3,5-DHBA | 13 | 9.7 | 0.94 | 1.05 |
| 4-HBA | 8.3 | 4 | 14.2 | 1.6 |

*Abbreviations: THBA = trihydroxybenzoic acid; DHBA = dihydroxybenzoic acid; HBA = hydroxybenzoic acid.

These data show that the TED adducts tested successfully catalyzed the hardening of the epoxy resin upon heating. Further, the data show that the TED adducts with 3,5-hydroxy-substituted benzoic acid and derivatives thereof (e.g. gallic acid) and with 2,3,4-trihydroxybenzoic acid and derivatives thereof unexpectedly provide superior latency for applications in which high latency and long pot lives are required. TED adducts with 4-hydroxybenzoic acid and derivatives thereof show the advantageous combination of intermediate latency and very high reactivity upon heating. Additionally, in the 55° C. aging testing, the TED adducts with 3,5-hydroxy-substituted benzoic acid derivatives and 2,3,4-hydroxy-substituted derivatives proved very highly latent. For example, the thermosettable Composition containing the TED-gallic acid adduct remained non-gelled for a period of 84+ days, retaining substantially the same viscosity values over this period. The TED-3,5-dihydroxybenzoic acid and TED-2,3,4-trihydroxybenzoic acid adducts remained non-gelled for a period of more than 24 days.

EXAMPLE III

Preparation of Bicyclic Amidine/BF₃ Complexes

The bicyclic amidine/BF₃ complexes were prepared as follows. A flask was equipped with a mechanical stirrer, reflux condenser, thermometer and an addition funnel, and was charged with the bicyclic amidine as a 50 wt % solution in tetrahydrofuran. This solution was cooled, using a wet ice bath, to 15° C. An equimolar amount of BF₃ etherate was added, dropwise, at such a rate that the reaction temperature did not exceed 20° C. The reaction mixture was stirred for one hour. The precipitated white solids were filtered, washed with cold tetrahydrofuran and then pentane, and were dried in a vacuum oven at 60° C. The yield of recovered product ranged from 70 to 80%. If a di complex was sought, he same procedure was used except two equivalents of BF₃ etherate were used and the reaction temperature was allowed to increase as the BF₃ etherate was added. The reaction mixture was then heated under reflux for one hour after the BF₃ etherate addition had been completed. The reaction mixture was cooled in a wet ice bath to <10° C. The reaction mixture was placed on a rotary evaporator and all of the solvents were removed to give an oil.

An alternate procedure for making the BF₃ complexes is to dissolve the bicyclic amidine in toluene to give a 50 wt % solution, and cool the solution to 10° to 15° C. An equimolar amount of anhydrous BF₃ is then bubbled into the solution maintaining a reaction temperature of less than 20° C. by using a wet ice bath. The reaction mixture is then stirred for 4 hours and the precipitated solids filtered, washed with some pentane, and dried in a vacuum oven at 60° C. Yields for this procedure are 60–65%.

Another procedure which can be used to prepare the $BF_3$ complexes is to dissolve the bicyclic amidine (0.26 mole) in toluene (100 ml) and cool the solution to less than 20° C. To this cooled solution is added BF etherate (0.26 mole), dropwise, holding the reaction temperature at less than 20° C. The reaction mixture is then stirred for one hour, and then heated until a solution resulted. The warm reaction mixture is then placed on a rotary evaporator and the solvent removed under vacuum, at 70° C. The resulting oil slowly solidifies upon cooling. The yields for the procedure are quantitative.

The following bicyclic amidine/$BF_3$ complexes, prepared by the first-specified procedure above, have the following characteristics:

DBU-$BF_3$, m.p. 86–88, Combustion analysis Actual (theory); C: 48.99 (49.13); H: 7.37 (7.33); N: 12.71 (12.73).

DBN-$BF_3$, m.p. 123.5–125, Combustion analysis Actual (theory); C: 43.65(43.79); H: 6.28 (6.30); N: 14.60 (14.59); F: 29.57 (29.69).

DBU-2 $BF_3$, m.p. N/A, Combustion analysis Actual (theory); C: 41.06 (37.55); H: 6.63 (5.60); N: 7.50 (9.73).

EXAMPLE IV

Testing of Bicyclic Amidine/$BF_3$ Complexes 1,5-Diazabicyclo[4.3.0]non-5-ene ("DBN") and 1,8-diazabicyclo[5.4.0]undec-7-ene ("DBU") were tested in the same manner as the compounds in Example II. The results are shown in Table 2.

TABLE 2

| Mono-$BF_3$ Complex with | /--Sunshine Gel Time--/ | | Heat Aged (55° C.) Latency Ratio | |
|---|---|---|---|---|
| | 120° C. | 150° C. | 3 day | 1 day |
| DBU | 31.3 | 8.0 | 1.03 | 0.98 |
| DBN | 83.7 | 13.0 | 1.00 | 1.0 |

These results demonstrate the superior latency and reactivity of the bicyclic amidine/$BF_3$ complexes. In the long term 55° C. aging testing, the thermosettable composition containing the DBU-$BF_3$ complex remained non-gelled for a period of 27 days, while the DBN-$BF_3$ complex shows a flat viscosity and remains non-gelled for 29+ days. Additionally, using the bicyclic amidine/$BF_3$ complexes, good quality, light-colored hardened resins were obtained, making these catalysts excellently suited for use in thermosettable coating compositions.

All publications cited herein are indicative of the level of ordinary skill in the art and are hereby incorporated by reference herein in their entirety as if each had been individually incorporated by reference.

While the invention has been illustrated and described in detail in the foregoing description, the same is to be considered as illustrative and not restrictive in character, it being understood that only the preferred embodiments have been described and that all changes and modifications that come within the spirit of the invention are desired to be protected.

What is claimed is:

1. A thermosettable composition, comprising a curable resin containing epoxy functionality and a catalytic amount of a mono-boron trifluoride complex with a bicyclic amidine compound having the formula:

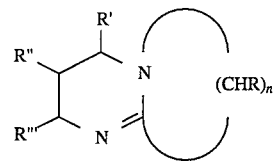

wherein n is a number ranging from 3 to about 7 nd R, R', R" and R"', which may be the same or which may differ from one another, are H or alkyl.

2. The thermosettable composition of claim 1 in which R, R', R" and R"' are each H.

3. The thermosettable composition of claim 2 which includes the mono-$BF_3$ complex of 1,5-diazabicyclo[4.3.0]non-5-ene or 1,8-diazabicyclo[5.4.0]undec-7-ene.

4. The thermosettable composition of claim 3 which includes the mono-$BF_3$ complex of 1,5-diazabicyclo[4.3.0]non-5-ene.

5. The thermosettable composition of claim 3 which includes the mono-$BF_3$ complex of 1,8-diazabicyclo[5.4.0]undec-7-ene.

6. The thermosettable composition of claim 1 wherein said boron trifluoride complex is present in about 1 to about 10 weight parts per 100 weight parts of said curable resin.

7. The thermosettable composition of claim 2 wherein said boron trifluoride complex is present in about 1 to about 10 weight parts per 100 weight parts of said curable resin.

8. The thermosettable composition of claim 3 wherein said boron trifluoride complex is present in about 1 to about 10 weight parts per 100 weight parts of said curable resin.

* * * * *

UNITED STATES PATENT AND TRADEMARK OFFICE
CERTIFICATE OF CORRECTION

PATENT NO. : 5,484,873
DATED : January 16, 1996
INVENTOR(S) : John R. Johnson

It is certified that error appears in the above-indentified patent and that said Letters Patent is hereby corrected as shown below:

On the Title page, item [54], please change "COMPOITIONS" to --COMPOSITIONS--.

In column 1, line 3, please change "COMPOITIONS" to --COMPOSITIONS--.

In column 1, line 24, please change "Co" to --to--.

In column 1, line 58, please change "88119031,8" to --88119031.8--.

In column 2, line 19, please add a semi-colon after "alkyl".

In column 2, line 46, please change "Dr" to --or--.

In column 2, line 59, please delete the second comma.

In column 3, line 48, please delete the second comma.

In column 5, line 53, please change "he" to --the--.

In column 6, line 27, please change "Composition" to --composition--.

In column 6, line 50, please change "he" to --the--.

In column 7, line 4, please change "BF" to --$BF_3$--.

In column 8, line 26, please change "nd" to --and--.

Signed and Sealed this

Fourteenth Day of May, 1996

Attest:

BRUCE LEHMAN

*Attesting Officer*     *Commissioner of Patents and Trademarks*